United States Patent [19]
Camino et al.

[11] Patent Number: 5,728,161
[45] Date of Patent: Mar. 17, 1998

[54] LARGE TAPER MODULAR SHOULDER PROSTHESIS

[75] Inventors: Thomas S. Camino; Duane G. Snyder; David J. Urbahns, all of Warsaw, Ind.

[73] Assignee: Depuy Orthopedics, Inc., Warsaw, Ind.

[21] Appl. No.: 488,585

[22] Filed: Jun. 8, 1995

[51] Int. Cl.$^6$ .................................................. A61F 2/40
[52] U.S. Cl. .................................................. 623/19; 623/18
[58] Field of Search .................................. 623/16, 18, 19, 623/22, 23

[56] References Cited

U.S. PATENT DOCUMENTS

| | | | |
|---|---|---|---|
| 4,005,495 | 2/1977 | Locke et al. | 623/23 |
| 4,032,994 | 7/1977 | Frey | 623/22 |
| 4,624,674 | 11/1986 | Pappas et al. | 623/22 |
| 4,865,605 | 9/1989 | Dines et al. | |
| 4,865,609 | 9/1989 | Roche | 623/23 |
| 4,919,670 | 4/1990 | Dale et al. | |
| 4,932,974 | 6/1990 | Pappas et al. | 623/16 |
| 4,995,883 | 2/1991 | Demane et al. | |
| 5,002,581 | 3/1991 | Paxson et al. | |
| 5,080,685 | 1/1992 | Bolesky et al. | 623/23 |
| 5,108,437 | 4/1992 | Kenna | |
| 5,108,452 | 4/1992 | Fallin | |
| 5,135,529 | 8/1992 | Paxon et al. | |
| 5,181,928 | 1/1993 | Bolesky et al. | 623/23 |
| 5,314,479 | 5/1994 | Rockwood, Jr. et al. | 623/19 |
| 5,358,526 | 10/1994 | Tornier | |
| 5,370,706 | 12/1994 | Bolesky et al. | |
| 5,489,309 | 2/1996 | Lackey et al. | |
| 5,507,817 | 4/1996 | Craig et al. | |
| 5,507,830 | 4/1996 | DeMane et al. | |

FOREIGN PATENT DOCUMENTS

| | | |
|---|---|---|
| 0 547 369 B1 | 5/1995 | European Pat. Off. |
| WO 95/22302 | 8/1995 | WIPO |

OTHER PUBLICATIONS

Frederick F. Buechel M.D., "Buechel–Pappas™ Total Shoulder System", Endotech, Inc., Jul., 1991.

Russell F. Warren, M.D. and David M. Dines M.D., "Bio–Modular® Total Shoulder",Biomet, Inc., 1992.

Charles A. Rockwood, Jr., M.D. and Frederick A. Matsen, III, M.D., "Global™ Total Shoulder Arthroplasty System", DePuy Inc., 1992.

"Buechel–Pappas™ Total Shoulder System Implants and Instruments", Endotec, Inc., Jul., 1991.

"Equipped to Preserve", DePuy–DuPont Orthopaedics, 1993.

Frederick A. Matsen, II, M.D. and Charles A. Rockwood, Jr., M.D., "Global™ Total Shoulder Arthroplasty System Design Rationale and Surgical Technique", DePuy Inc., 1992.

Primary Examiner—David Isabella
Attorney, Agent, or Firm—Barnes & Thornburg

[57] ABSTRACT

A joint prosthesis including a first element comprising a joint bearing surface and a second element which has an integral stem and body portion. The body includes a collar having a male taper outer surface configured to engage a complementary female taper surface formed in the joint bearing surface of the first element. Engagement of the female taper on the male taper provides the sole mechanical connection between the joint bearing member and the stem body element. The invention includes a kit for assembly of a modular joint prosthesis, the kit includes at least two stem body elements and at least two joint bearing members.

10 Claims, 4 Drawing Sheets

U.S. Patent     Mar. 17, 1998     Sheet 1 of 4     5,728,161
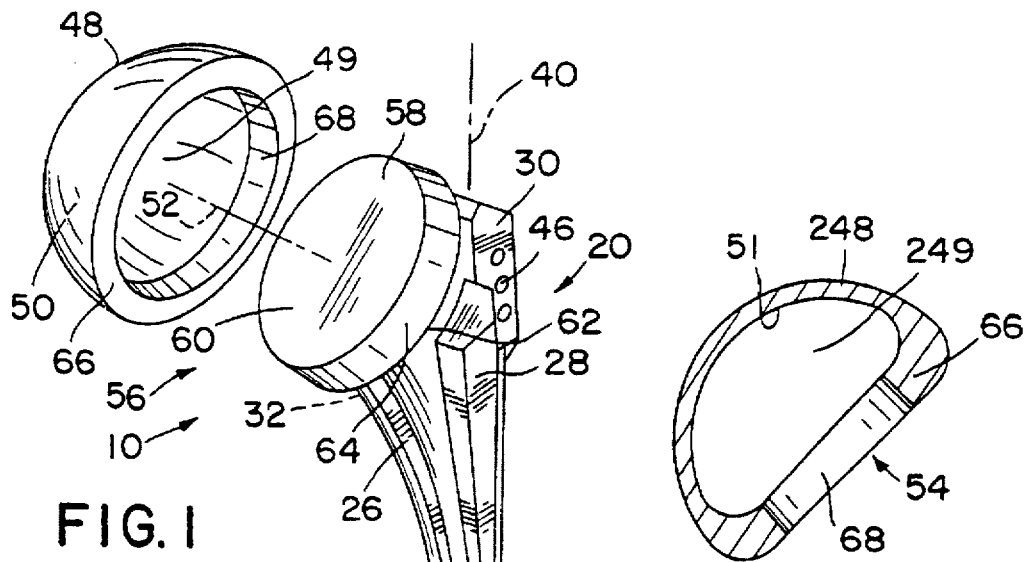
FIG. 1
FIG. 4
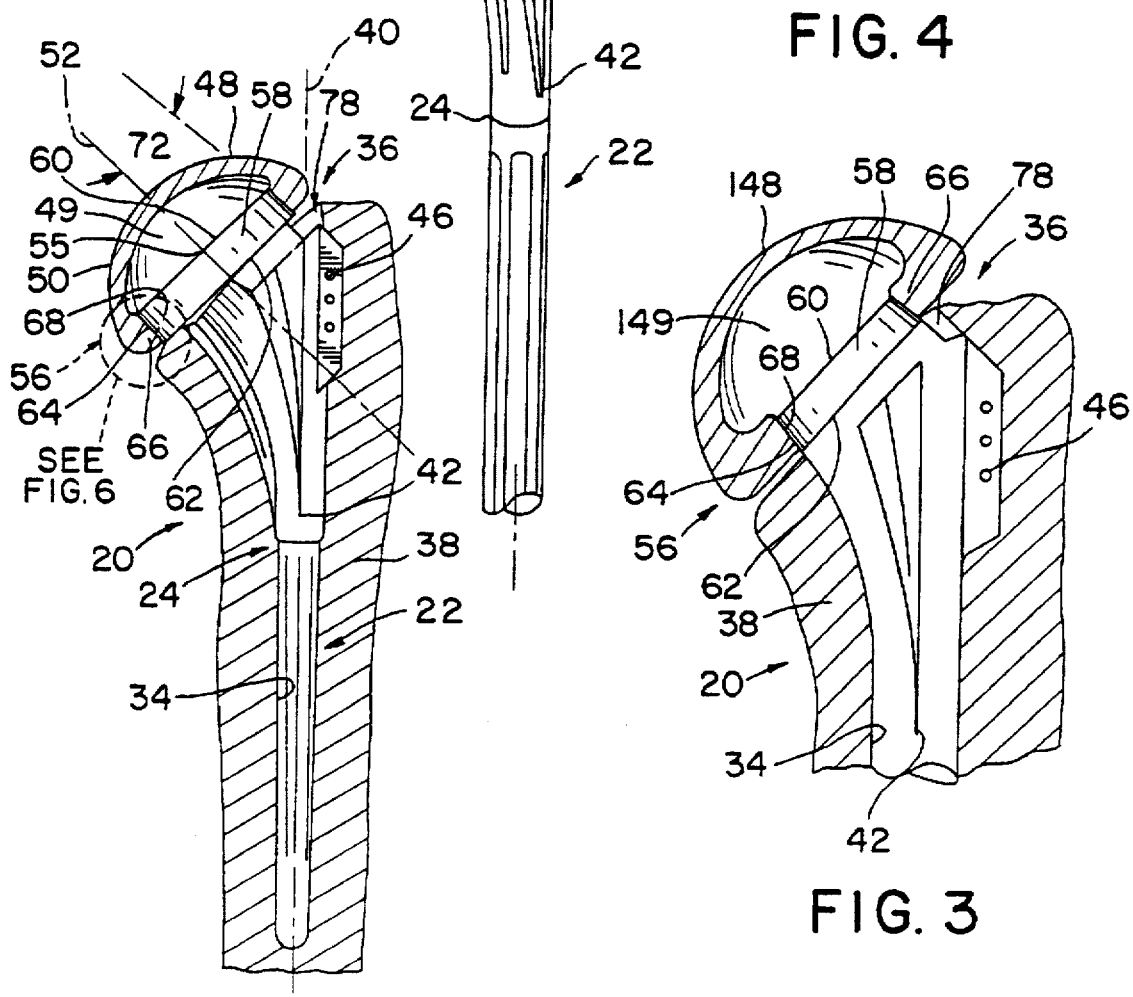
FIG. 2
FIG. 3

LARGE TAPER MODULAR SHOULDER PROSTHESIS

This invention relates to improvements in joint prostheses. It is disclosed in the context of a shoulder prosthesis but is believed to have utility in other applications as well.

There are a number of prostheses which employ, as part of their systems for joining prosthesis components, tapered locking joints such as Morse tapered joints and the like. There are also the systems illustrated and described in U.S. Pat. Nos.: 5,080,685; 5,181,928; 5,314,479; 4,932,974; and 4,624,674; European Patent Specification 0,547,369 B1; Buechel-Pappas™ Total Shoulder System Implants and Instruments; and, Buechel-Pappas™ Total Shoulder System Surgical Procedure by Frederick F. Buechel M. D. No representation is intended hereby that a thorough search of all material prior art has been conducted or that no more material prior art exists. Nor should any such representation be inferred. The disclosures of the '685, '928 and '479 patents are incorporated herein by reference.

A significant concern in the design of joint prostheses is weight. Particularly the bearing surfaces of such prostheses must be made of durable materials, with such alloys as cobalt chrome being preferred by many physicians. Titanium, while it is lighter, is not as durable and so, for many of the prosthetic joint bearing surfaces is not an acceptable substitute. The generally competing desires for light weight and durability have led to a number of multiple component prostheses. In such prostheses, components which do not provide bearing surfaces are fabricated from somewhat less durable but typically more lightweight materials such as, for example, titanium. Components which provide bearing surfaces are fabricated from somewhat more durable but typically heavier weight materials such as, for example, cobalt chrome. A problem with many such prostheses, however is that they are designed without optimal regard for the durability-weight tradeoffs. Consequently, many of the bearing components are designed for greater strength than is necessary under the circumstances. An example would be a shoulder prosthesis, the head portion of which is constructed from cobalt chrome and the body/shank portion of which is made from titanium alloy. Although the head is constructed from extremely durable cobalt chrome, it is a thick-walled component, making it rather heavier than necessary to perform its bearing function. Its thick-walled design is related in part to the manner in which it is joined to the body/shank portion of the shoulder prosthesis. Usually this involves multiple butt joint and/or tapered surfaces and threaded fasteners, all of which add to the weight of the prosthesis.

Another significant consideration in the design of such joint prostheses is range of motion. Designs strive to achieve the natural range of motion of a healthy joint. The techniques by which the various components of the prosthesis, such as the head portion and body/shank portion in the shoulder prosthesis example described above, are joined clearly affect the range of motion available in such a prosthesis. In some of the shoulder joint prostheses identified in the above-noted prior art, for example, some potential bearing surface on the head of the humeral component is lost by the choice of techniques for connecting the head portion to the body/shank portion of the humeral component.

It is an object of the invention to provide a lighter weight configuration for a prosthesis.

It is another object of the present invention to provide a design for a multiple component joint prosthesis which makes more effective use of potentially available joint bearing surface.

According to an aspect of the invention a kit for assembly of a modular joint prosthesis for replacement of a head, neck and adjacent portions of a bone of the joint comprises at least two stem body elements. Each element is sized for insertion into the shank of the bone. At least two head members are provided. Each head member is sized to replace one of the bearing surfaces of the joint. Each stem body element comprises an upper collar which lies adjacent the resected level of the bone in the completed prosthetic joint. The collar provides a male taper at its outer diameter. Each head member provides a complementary female taper for receiving the male taper of each stem body element. Engagement of the female taper on the male taper provides the sole mechanical connection between the head and the stem body element.

According to another aspect of the invention, a joint prosthesis consists essentially of an integral stem and body. The body includes a collar having a male taper toward a complementary bearing surface to the prosthesis, and a head having a female taper complementary to the male taper of the collar to receive the collar in the assembled joint.

According to another aspect of the invention, a joint prosthesis comprises a first component and a second component. The second component consists essentially of an integral stem and body. The body includes a collar having a male taper toward the first component in the assembled joint, and a head having a female taper complementary to the male taper of the collar to receive the collar in the assembled joint.

According to another aspect of the invention, a joint prosthesis assembly for replacement of a head, neck, and adjacent portion of a first bone of the joint removed at a resected level comprises a stem-body element for insertion into the resected first bone. The element comprises a body portion with a stem portion extending downwardly to be received in a shank of the first bone and a collar portion to be adjacent the resected level. The collar portion has a radially outer peripheral surface formed to provide a peripheral engaging surface extending away from the resected level toward an opposite bearing surface of a second bone of the joint. A head member provides a spherical outer bearing surface facing the opposite bearing surface and an inner surface having, at its radially outer extent, a corresponding peripheral surface for engaging the collar engaging surface after the stem-body element is installed in the shank of the bone. The engaging surfaces provide the sole mechanical connection between the head member and the stem-body element.

The invention may best be understood by referring to the following description and accompanying drawings which illustrate the invention. In the drawings:

FIG. 1 illustrates a fragmentary exploded perspective view of an apparatus constructed according to the invention;

FIG. 2 illustrates a fragmentary longitudinal sectional view through the apparatus of FIG. 1 assembled;

FIG. 3 illustrates a fragmentary longitudinal sectional view through an apparatus according to the present invention;

FIG. 4 illustrates a longitudinal sectional view of an alternative detail to a detail of the apparatus illustrated in FIGS. 1–3;

Figure 8:
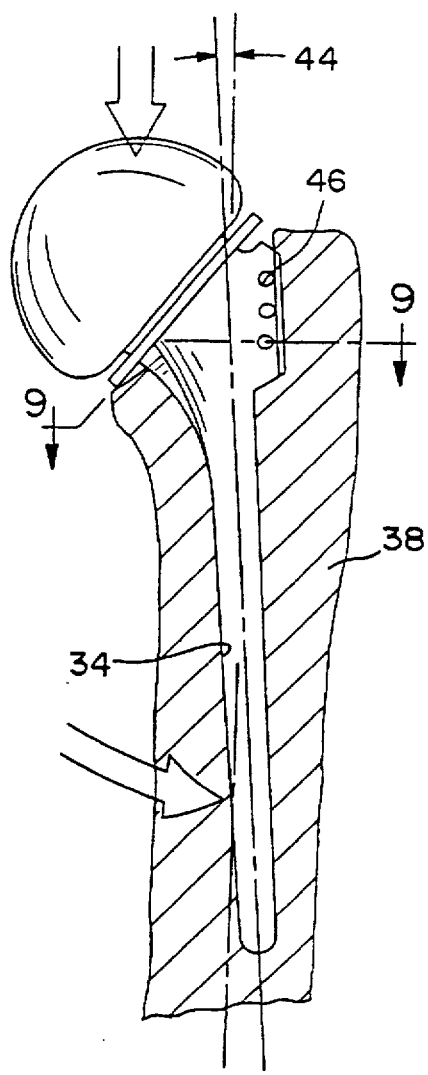
FIG. 8 illustrates a fragmentary longitudinal sectional view through a prior art device illustrating a problem addressed by the present invention.
Figure 11:
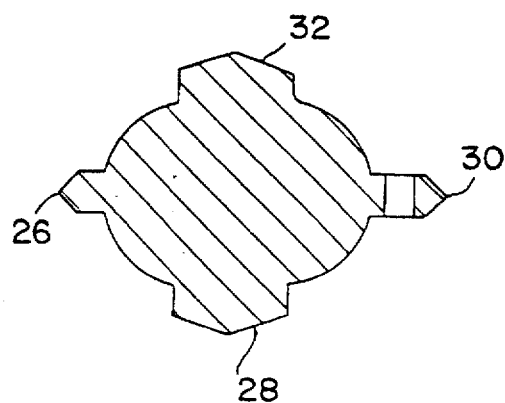
FIG. 11 illustrates a fragmentary section view, taken generally along section lines 11—11 of FIG. 10.
Figure 9:
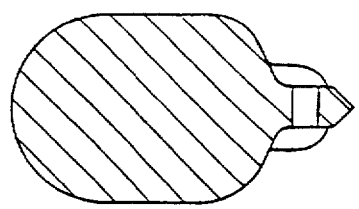
FIG. 9 illustrates a fragmentary sectional view, taken generally along section lines 9—9 of FIG. 8.

Referring now to FIGS. 1–2, a shoulder prosthesis includes a humeral body portion 20 and shank portion 22. The shank portion 22 can be formed integrally with, or as a separate component from the body portion 20. If the two portions 20, 22 are formed separately any suitable means such as welding, soldering, threaded engagement, either with or without (a) suitable adhesive(s), or the like can be used to join them together at a joint 24. The body portion 20 is provided with ribs 26, 28, 30 and 32 for guiding the humeral body 20 and shank 22 as they are inserted into the medullary passageway 34 from the prepared proximal end 36 of the humerus 38. Ribs 26 and 30 are generally straight sided ribs that extend generally parallel to the centerline 40 of shank 22. Ribs 28 and 32 on the other hand are somewhat wedge-shaped, each larger adjacent the proximal end 36 of humerus 38 and tapering generally to a point 42 distally therefrom. This feature reduces the tendency, illustrated in FIGS. 8–9, of prior art humeral components to become tilted 44 in a varus-valgus direction during insertion into the medullary passageway 34 in the humerus 38. One or more of ribs 26, 28, 30, 32 can be provided with suture openings 46 in accordance with current practice. These are useful in the repair of certain kinds of injuries and disease. The stem/body portion 22, 20 illustratively is constructed from relatively lighter weight, relatively less durable material such as titanium.

The humeral component is also provided with a part spherically shaped head portion 48. The required portion 50 of a spherical surface defined by head 48 varies from person to person and for this reason, kits containing a number of shallower and deeper head portions 48, 148, 248 and so on can be provided in kits. For this same reason, such kits can contain more than one stem/body portion 22, 20; 122, 120; 222, 220 and so on. Alternatively, if a detachable body 20, 120, 220/stem 22, 122, 222 configuration is employed different numbers (for example, only one) of body(ies) 20, 120 and stems 22, 122, 222 can be provided. The head portions 48, 148, 248 ... illustratively are constructed from more durable material such as, for example, a cobalt chromium alloy. Although such materials typically are somewhat heavier, weight is optimized by the thin wall construction of heads 48, 148, 248 ... with their attendant generally part spherical cavities 49, 149, 249 ....

In any event, a standard attachment mechanism 56 is provided for the attachment of any head portio 48, 148, 248 ... to the body 20, 120, 220 ... of any stem/body portion 22/20, 122/120 .... Attachment mechanism 56 includes a collar 58 of uniform size and configuration formed at the proximal end of each stem/body portion 22/20, 122/120 ..

Figure 6:
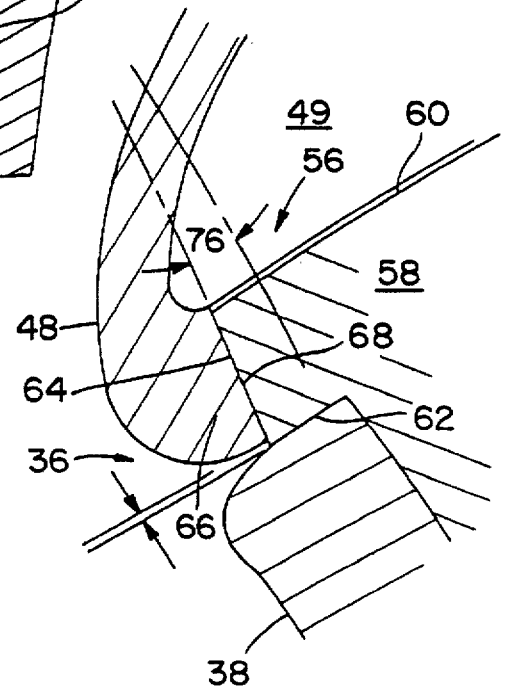
FIG. 6 illustrates a much enlarged fragmentary longitudinal sectional view through an apparatus according to the invention.
Figure 7:
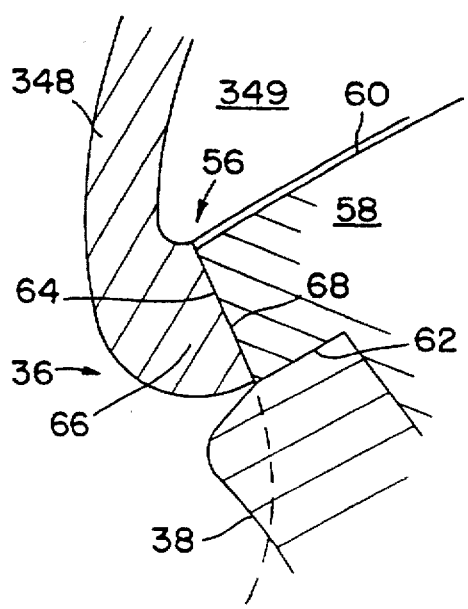
FIG. 7 illustrates a fragmentary longitudinal section view of an alternative detail to the detail illustrated in FIG. 6.

.. The illustrated collars 58 are circular in plan view with a smaller circle 60 more proximal to the glenoid and a larger circle 62 more remote from the glenoid in an assembled prosthetic joint. The sidewall 64 of each collar 58 thus is characterized by an exterior or mole taper. The taper may be a straight taper, as in FIGS. 1–3, 5 and 6, or it may be curved, for example, exponential, a curve of a conic section-circle, ellipse, parabola, hyperbola) or the like, as illustrated in FIG. 7. The head portions 48, 148, 248 ... of any kit are provided with skirts 66. The skirts 66 have walls 68 providing complementary interior or female tapers. In other words if the tapers of walls 64 in any kit are straight, the tapers of the walls 68 of the head portions 48, 148, 248 ... in that kit are also straight. If one set 64 of tapers are parabolic sections, the other set 68 of tapers are complementary parabolic sections, and so on. The tapers 64, 68 are locking tapers. That is, in the case of straight, symmetric tapers, the included angle between diametrically opposite points on the collar 58 will be greater than zero degrees and less than or equal to fourteen degrees. Referring to FIG. 2, which illustrates a symmetrically tapered wall 64, the angle 72 between the concentric centerlines 74 of circles 60, 62 and wall 64 is greater than zero degrees and less than or equal to seven degrees, as is the angle 76 in FIG. 6. When a curved taper is employed, as in FIG. 7, a locking taper can be achieved if the acute angles between tangents to the curve over much of its length and perpendicular to the surfaces 60, 62 are greater than zero degrees and do not exceed seven degrees.

Figure 5:
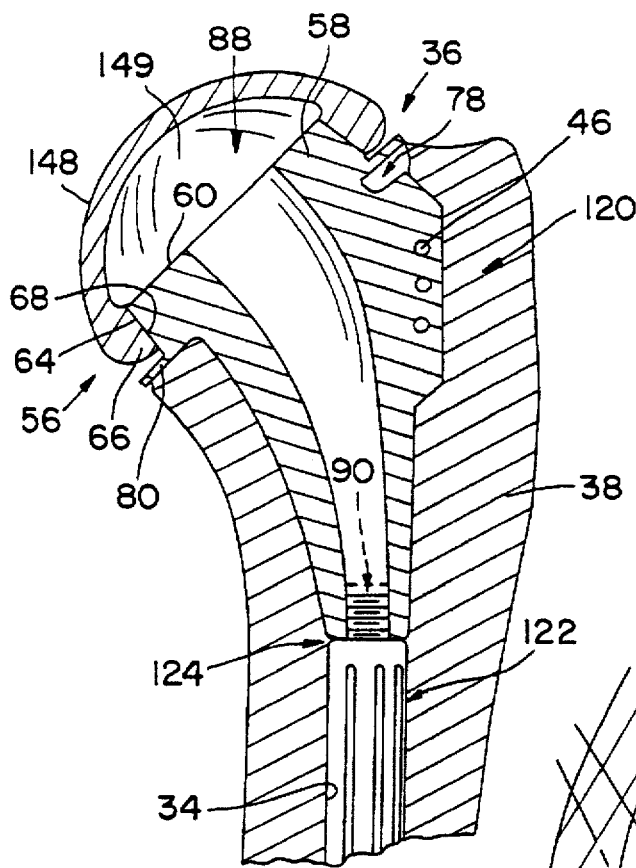
FIG. 5 illustrates a fragmentary longitudinal sectional view through an apparatus according to the present invention.
Figure 10:
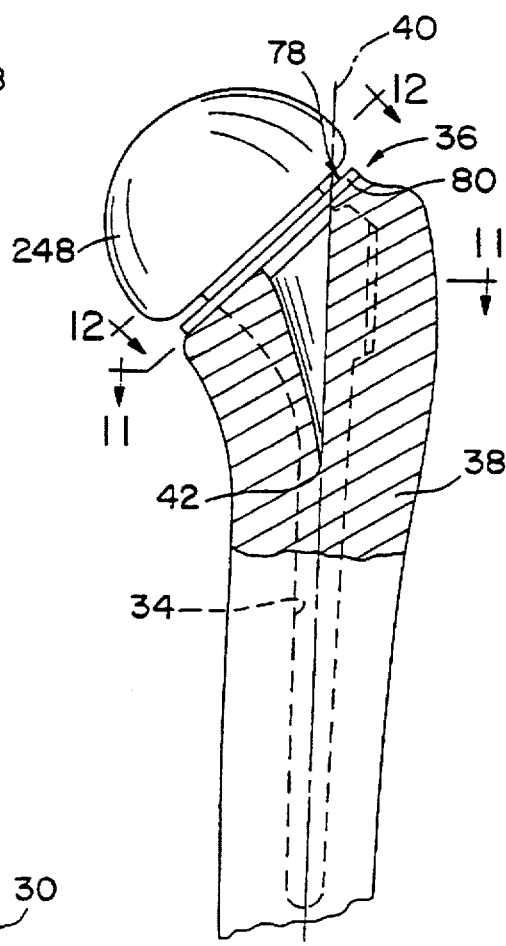
FIG. 10 illustrates a fragmentary longitudinal sectional view of an apparatus constructed according to the invention.
Figure 12:
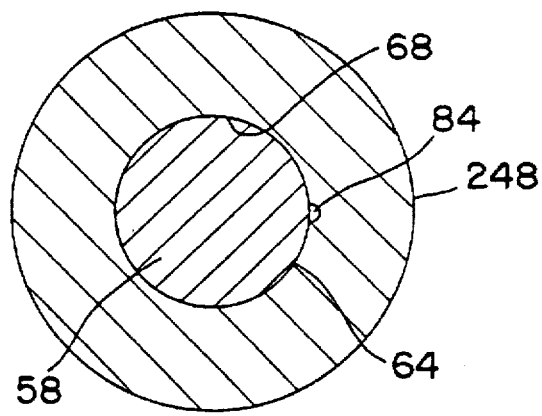
FIG. 12 illustrates a fragmentary sectional view, taken generally along section lines 12—12 of FIG. 10.
Figure 12A:
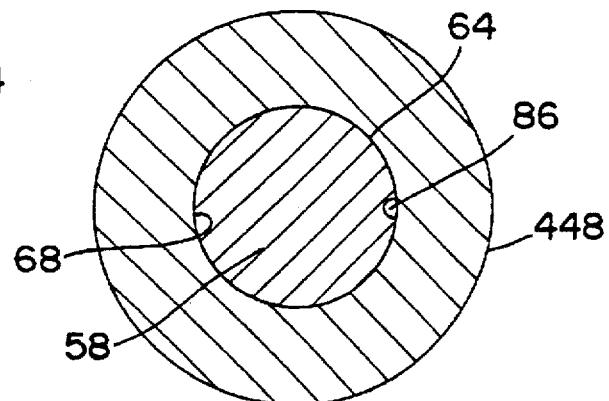
FIG. 12a illustrates an alternative detail to the detail illustrated in FIG. 12.
Figure 14:
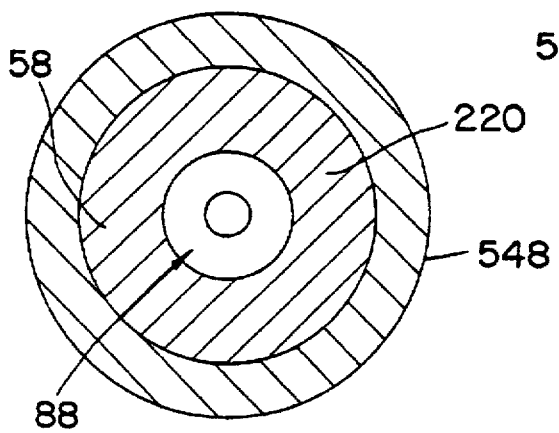
Figure 13:
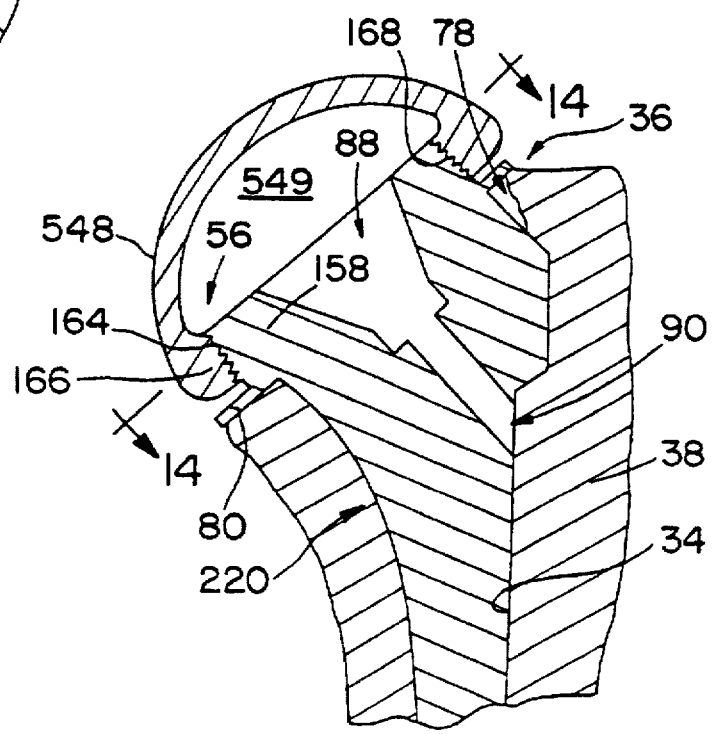
FIG. 13 illustrates a fragmentary longitudinal sectional view of an alternative detail to the details illustrated in FIGS. 11, 12 and 12a; and, FIG. 14 illustrates a fragmentary sectional view taken generally along section lines 14—14 of FIG. 13.

Referring now to FIGS. 5, 10 and 13, in the preparation of the proximal end 36 of humerus 38 to receive a prosthesis according to the invention, the proximal end is resected as illustrated at 78. The surface 62 of collar 58 lies adjacent surface 78 when the stem/body portion 22/20, 122/120 ... is inserted into the humerus 38. The collar 58 generally will be thick enough to permit full engagement of the wall 68 with a portion of wall 64. This will prevent interference of proximal end 36 of humerus 38 with skirt 66 and insure maximum retention of head portion 48, 148 ... on collar 58. This can further be insured by provision of an illustratively circular flange 80 adjacent collar 58. The stem/body portion 22/20, 122/120 ... is inserted into the humerus 38 until it is stopped by interference of the flange 80 with end 36 of humerus 38.

Referring now to FIGS. 5, 12, 12a, 13 and 14, venting of the cavity 49, 149, 249 ... during installation of head portion 48, 148, 248 ... onto collar 58 is achieved by providing one or more of a discontinuity 84 in wall 68 (FIG. 12), a discontinuity 86 in wall 64 (FIG. 12a), and a passageway 88, 188 through collar 58 from surface 60 to a remote location 90, 190 on stem/body portion 22/20, 122/120 ....

Alternative forms of standard attachment mechanism 56 are contemplated. For example, and as illustrated in FIG. 13, complementary threads 164, 168 are provided on the outer wall of collar 158 and the inner wall of skirt 166, respectively.

What is claimed is:

1. A kit for assembly of a modular joint prosthesis for replacement of a head, neck and adjacent portions of a bone of the joint, the kit comprising, at least two stem body elements, with each element of said at least two stem body elements sized for insertion into the shank of the bone, and at least two head members with each head member of said at least two head members sized to replace one of the bearing surfaces of the joint, each stem body element of said at least two stem body elements comprising an upper circular collar to be superimposed on a resected level of the bone, said collar providing a male taper at its outer diameter, each head member of said at least two head members providing a corresponding female taper for receiving the male taper of each stem body element of said at least two stem body elements, the engagement of the female taper on the male taper providing a mechanical connection between each head member of said at least two head members and a stem body element of said at least two stem body elements, and wherein said collar terminates above said male taper and in which each said head member is formed with a generally spherical concave inner surface providing, at its radially outer extent, said female taper to define above said collar a hollow space, said stem-body element and said head member cooperating to define a passageway for venting said hollow space.

2. A kit for assembly of a modular joint prosthesis for replacement of a head, neck and adjacent portions of a bone of the joint, the kit comprising, at least two stem body elements, with each element of said at least two stem body elements sized for insertion into the shank of the bone, and at least two head members with each head member of said at least two head members sized to replace one of the bearing surfaces of the joint, each stem body element of Said at least two stem body elements comprising an upper circular collar to be superimposed on a resected level of the bone, said collar providing a male taper at its outer diameter, each head member of said at least two head members providing a corresponding female taper for receiving the male taper of each stem body element of said at least two stem body elements, the engagement of the female taper on the male taper providing a mechanical connection between each head member of said at least two head members and a stem body element of said at least two stem body elements, wherein, the kit is a kit for assembly of a modular shoulder prosthesis for replacement of a head, neck and adjacent portions of a humerus, and wherein said head member has a spherical outer bearing surface facing the glenoid of the shoulder and a generally spherical inner surface to provide a head member having a thin walled spherical wall section, said generally spherical inner surface terminating, at its radially outer extent, with said female taper.

3. A joint prosthesis consisting essentially of an integral stem and body, the body including a collar having a male taper toward a complementary bearing surface for the integral stem and body, and a head having a complementary female taper corresponding to the male taper of the collar to receive the collar in the assembled joint, and wherein the taper is symmetrical.

4. A joint prosthesis consisting essentially of an integral stem and body, the body including a collar having a male taper toward a complementary bearing surface for the integral stem and body, and a head having a complementary female taper corresponding to the male taper of the collar to receive the collar in the assembled joint, wherein the male taper is provided with a discontinuous section to provide a passageway through the collar to vent a space defined between the collar and head in an assembled configuration.

5. A joint prosthesis consisting essentially of an integral stem and body, the body including a collar having a male taper toward a complementary bearing surface for the integral stem and body, and a head having a complementary female taper corresponding to the male taper of the collar to receive the collar in the assembled joint, wherein the female taper is provided with a discontinuous section to vent a space defined between the collar and head in an assembled configuration.

6. A joint prosthesis consisting essentially of an integral stem and body, the body including a collar having a male taper toward a complementary bearing surface for the integral stem and body, and a head having a complementary female taper corresponding to the male taper of the collar to receive the collar in the assembled joint, wherein a space is defined between a top portion of the collar and a lower portion of the head in the assembled configuration of the two tapers and wherein the body and stem include a vent passageway extending between the space and a location on the stem remote from the head.

7. A joint prosthesis comprising a first component and a second component, the second component consisting essentially of an integral stem and body, the body including a collar having a male taper facing toward the first component in the assembled joint, and a head having a complementary female taper corresponding to the male taper of the collar to receive the collar in the assembled joint, and wherein the two tapers are symmetrical.

8. A joint prosthesis comprising a first component and a second component, the second component consisting essentially of an integral stem and body, the body including a collar having a male taper facing toward the first component in the assembled joint, and a head having a complementary female taper corresponding to the male taper of the collar to receive the collar in the assembled joint, and wherein the male taper is discontinuous to vent a space defined between the collar and head in an assembled configuration.

9. A joint prosthesis comprising a first component and a second component, the second component consisting essentially of an integral stem and body, the body including a collar having a male taper facing toward the first component in the assembled joint, and a head having a complementary female taper corresponding to the male taper of the collar to receive the collar in the assembled joint, and wherein the female taper is discontinuous to vent a space defined between the collar and head in an assembled configuration.

10. A joint prosthesis comprising a first component and a second component, the second component consisting essentially of an integral stem and body, the body including a collar having a male taper facing toward the first component in the assembled joint, and a head having a complementary female taper corresponding to the male taper of the collar to receive the collar in the assembled joint, and wherein a space is defined between the collar and head in the assembled configuration and the body and stem define a vent passageway extending between the space and a location on the stem remote from the head.

* * * * *